United States Patent

Ezure et al.

[11] Patent Number: 5,041,544
[45] Date of Patent: Aug. 20, 1991

[54] METHOD OF MANUFACTURING MORANOLINE DERIVATIVES

[75] Inventors: Yoji Ezure, Otsu City; Katsunori Miyazaki; Makoto Sugiyama, both of Kyoto, all of Japan

[73] Assignee: NipponShinyaku Co., Ltd., Japan

[21] Appl. No.: 39,011

[22] Filed: Apr. 15, 1987

[30] Foreign Application Priority Data

Apr. 15, 1986 [JP] Japan .................. 61-087508

[51] Int. Cl.$^5$ ............................................. C07H 1/00
[52] U.S. Cl. ................... 536/127; 536/18.7; 536/55.3; 536/124
[58] Field of Search ............ 536/124, 127, 55.3, 536/18.7

[56] References Cited

U.S. PATENT DOCUMENTS 4,361,701 11/1982 White .................. 536/16.8
4,652,640 3/1987 Sakai et al. .................. 536/127

Primary Examiner—Elli Peselev
Attorney, Agent, or Firm—Rosenman & Colin

[57] ABSTRACT

A method of preparing crystals of a glucosylmoranoline formula (III)

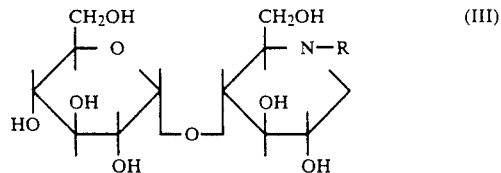

wherein R is hydrogen or lower alkyl by fractional cyrstallizatin using a polar solvent and an arylsulfonic acid.

12 Claims, No Drawings

METHOD OF MANUFACTURING MORANOLINE DERIVATIVES

The present invention relates to a method of preparing crystals of a glucosylmoranoline represented by the general formula (III)

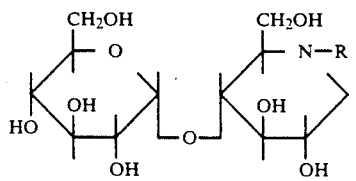

wherein R is hydrogen or lower alkyl. Preferably, R is branched or straight chain alkyl having from about 1 to about 8 carbon atoms, most preferably from about 1 to about 5 carbon atoms. Compound (III) has excellent inhibitory action against blood sugar increase when administered to a sugar-loaded animal and is useful in the treatment of diabetes mellitus (cf. Japanese Laid Open Publication 56/081595 etc.)

It has been previously proposed to make (III) by contacting an aqueous solution comprising a moranoline derivative represented by the general formula (I)

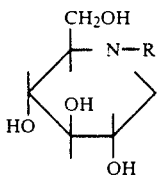

wherein R is as defined above and cyclodextrine or soluble starch with cyclodextrin glycosyltransferase (EC 2.4.1.19) to form a mixture of (III) and an oligoglucosylmoranoline derivative represented by the general formula (II)

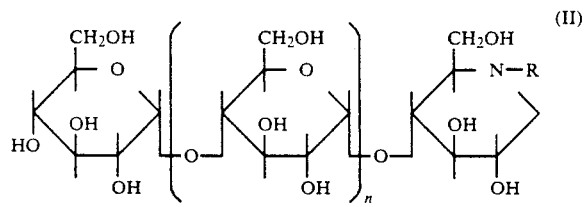

wherein R is as defined above and n is an integer of 1 to about 20. The reaction product contains unreacted (I) and by-product (II) in addition to the desired product (III), the ratio of these compounds varying depending upon the reaction conditions. Accordingly, the reaction product had to be worked up to isolate and purify (III).

In accordance with another proposal, compound (II) can be converted to (III) in high yield by treating the above reaction product with glucoamylase (alpha-1,4-glucanglucohydrolase EC 3.2.1.3) (cf. Japanese Laid Open Publication 57/058890). Although this is a good method of manufacture, unreacted (I) is still present and, in addition, a small amount of (II) is also obtained under certain reaction conditions.

To recover the desired compound (III), it was necessary to employ molecular weight fractionation using Sephadex or the like or a column chromatography of reversed phase type using Lichroprep CN (Registered Trademark; Merck Co) or Micro Bondapak-NH₂ (Registered Trademark; Waters Co). However, column operations require much time, are costly and are difficult to carry out.

It is an object of the present invention to provide a method of obtaining pure (III) from a mixture of (I), (II) and (III) in high yield.

It is another object of the present invention to provide a method of obtaining purified (III) of consistent quality.

Accordingly, the present invention provides a method of obtaining (III) from a mixture of (I) and (III) or (I), (II) and (III), wherein the mixture is dissolved in a polar solvent, an arylsulfonic acid as such or a solution thereof in a suitable solvent is added thereto, and the crystals separated therefrom are collected. This method is based upon the discovery that when an arylsulfonic acid is added with the polar solvent to the mixture, compound (III) is first crystallized out before (I) and (II), thereby enabling the isolation of (III) from the mixture.

While fractional cyrstallization has previously been used by us in Japanese Patent Application 59/237326, the present invention represents a significant technical advance in the art.

The method of the present invention may be considered as a means for obtaining a specific sugar from a mixture of oligosugars. As is known, fractional crystallization of sugars is very difficult. Indeed the separation of maltose from a mixture of glucose, maltose and maltotriose is impossible. While prior proposals have been made to separate a single sugar from a mixture of sugars, such as by Sephadex column chromatography, carbon column chromatography, or a method using alkali metal or alkali earth metal type strongly acidic cationic exchange resin column chromatography, these prior proposals are quite difficult to carry out.

The polar solvent used in the present invention may be any suitable polar solvent, such as water, a lower alkanol, such as methanol, ethanol, isopropanol or the like. Polar solvents may be used alone or in admixture. Preferably, the polar solvent is water-miscible.

The arylsulfonic acids used in the present invention include substituted, such as alkyl-substituted, or unsubstituted benzenesulfonic acids, alkyl-substituted or unsubstituted dicyclic or tricyclic arylsulfonic acids and the like. The use of substituted or unsubstituted benzenesulfonic acids and lower alkyl substituted benzenesulfonic acids, such as is especially preferred, such as benzenesulfonic acid, p-toluenesulfonic acid, 2,4-dimethylbenzenesulfonic acid, and the like.

It is an advantage of the present invention that the temperature need not be raised or lowered after dissolving the mixture of (I) and (III) or (I), (II) and (III) in the polar solvent unlike conventional fractional crystallization methods. Generally, (III) is apt to be decomposed when heated in an acidic condition to give (I) and, accordingly, the absence of heating is a most advantageous feature of the present invention.

In carrying out the present invention, the mixture of (I) and (III) or (I), (II) and (III) may, for example, be dissolved or suspended in the polar solvent with heating or at room temperature followed by addition of another polar solvent for dissolution of the suspension. After the mixture is dissolved, the arylsulfonic acid is added at room temperature, the solution is allowed to stand for a period of time so that crystals are crystallized out therefrom, and the crystals can be collected, for example, by filtration, and they may be recrystallized, if necessary.

The resulting crystals are treated in a known manner to remove the arylsulfonic acid, such as by using a strongly basic ion exchange resin.

In accordance with the present invention, the yield, purity, etc. may vary greatly depending upon the conditions applied but, under optimum conditions, the desired compound (III) can be obtained from a mixture of (I), (II) and (III) in a yield of not lower than 97.2% and in a purity not lower than 98.7% by a single fractional crystallization step. Accordingly, when the method of the present invention is repeated, it is possible to afford pure crystals in a purity of as high as 99.97 to 100%.

The yield is higher when R is methyl than when R is hydrogen in (III). Therefore, the method of the present invention is useful when the N-unsubstituted compound (III) (wherein R is hydrogen) is methylated to form compound (III) wherein R is methyl.

The theory of operation of the present invention is not fully understood. However, it is believed that the moranoline derivatives form quaternary amine salts with the arylsulfonic acids in a polar solvent and, accordingly, it is believed that there is a difference in solubilitites of those salts in the polar solvent and that this provides for the selective crystallization of the method of the present invention.

The method of the present invention is industrially useful, because compound (III) is obtained in a highly pure crystalline form, as required for pharmaceuticals.

The present invention is further illustrated by way of the Reference Examples and Working Examples.

REFERENCE EXAMPLE 1

(1) Moranoline (8.5 g) was dissolved in a small amount of water and the solution was adjusted to pH 5.7 with 6N hydrochloric acid. Then water was added thereto to make 50 ml. Alpha-Cyclodextrine (34 g) was dissolved in 2330 ml of crude enzyme solution of 1000 units/ml of cyclodextrine glycosyltransferase and then aqueous solution of moranoline was added thereto to readjust to pH 5.7. This was shaken at 40° C. for two days to conduct the reaction. The reacted solution was centrifuged and the supernatant liquid was passed through a column of 100 ml of Dowex 50W×2 (H+) to adsorb the basic substances. The column was thoroughly washed with water, eluted with 0.5N ammonia water, and the eluate was concentrated to dryness in vacuo to give 42.0 g of mixed oligoglucosylmoranolines powder.

(2) The above oligoglucosylmoranolines powder (42.0 g) was dissolved in a small amount of water and the solution was adjusted to pH 5.1 with 6N hydrochloric acid. This was diluted to 4370 ml by addition of water. To this was added 250 mg of glucoamylase (Seikagaku Kogyo KK: 30 units/mg) and the mixture was made to react by stirring at 50° C. for 24 hours. The reaction solution was filtered and the filtrate was passed through Dowex 50W×2 (H+) (100 ml) so that the basic substance was absorbed therein. This was thoroughly washed with water, eluted with 0.5N ammonia water, and the eluate was treated with activated carbon followed by a concentration/drying in vacuo to give 18.6 g of powder.

This was subjected to a high performance liquid chromatography analysis and found to be composed of 14% of moranoline, 84% of 4-O-alpha-D-glucosyl-moranoline, and 2% of 4-O-alpha-D-maltosylmoranoline.

The conditions used for the high performance liquid chromatography were as follows:

Sumipax R 741 (Nucleosil 5NH$_2$, 5 micrometers; 4 mm ID×25 cm); developer: acetonitrile-water (65:35); flow rate: 1 ml/min; RI detection (by an ERC-7510 manufactured by Elmer Kogyo KK); Data processor (by model 655-60 manufactured by Hitachi Ltd).

REFERENCE EXAMPLE 2

(1) N-Methylmoranoline (10 g) was dissolved in a small amount of water and the solution was adjusted to pH 5.7 with 3N hydrochloric acid. Soluble starch (640 g) was dissolved in 7550 ml of hot water, the solution was cooled to 40° C., and the aqueous solution of N-methylmoranoline was added thereto. Then 400 ml of crude enzyme solution of 2000 units/ml of cyclodextrine glycosyltransferase was mixed therewith and the mixture was readjusted to pH 5.7. The mixture was shaken at 40° C. for 2 days to conduct the reaction. After the reaction, the temperature was adjusted to 50° C., then adjusted to pH 5.2 with concentrated hydrochloric acid, and 1 g of glucoamylase (Glucozyme AF6) was added followed by stirring at 50° C. for 24 hours to conduct the reaction. The reaction solution was centrifuged and the supernatant liquid was passed through a column of Dowex 50W×2 (H+) (the amount of the resin: 300 ml) so that the basic substance was adsorbed therewith. This was thoroughly washed with water, eluted with 0.5N ammonia water, the eluate was concentrated and dried in vacuo, then dissolved in methanol, the solution was treated with active carbon, and concentrated in to give 16.7 g of powder.

This was analyzed by a high performance liquid chromatography in the same manner as in Reference Example 1 and was found to be composed of 37.2% of N-methylmoranoline and 62.8% of 4-O-alpha-D-glucosyl-N-methylmoranoline.

REFERENCE EXAMPLE 3

Soluble starch (24 g) was dissolved in 280 ml of hot water and a solution of 1146 mg of N-ethylmoranoline in 5 ml of water (followed) by adjusting to pH 5.7) was added thereto. This was cooled to room temperature, 15 ml of crude enzyme solution of 2000 units/ml of cyclodextrine glycosyltransferase was added thereto, and the mixture was readjusted to pH 5.7. This was made to react by shaking at 40° C. for 3 days. After the reaction, it was adjusted to pH 5.2 with concentrated hydrochloric acid, then 75 mg of glucoamylase (Glucozyme AF-6) was added thereto, and the mixture was made to react at 50° C. for 24 hours. The reaction solution was centrifuged and the supernatant liquid was passed through a column of Dowex 50W×2 (H+) (amount of the resin: 60 ml) so that the basic substance was adsorbed therewith. This was thoroughly washed with water, eluted with 0.5N ammonia water, the eluate was concentrated and dried in vacuo, then dissolved in methanol, the methanolic solution was treated with active carbon and concentrated/dried in vacuo to give 2.3 g of powder.

This was analyzed by high performance liquid chromatography in the same as in Reference Example 1 and was found to be composed of 19% of N-ethylmoranoline and 81% of 4-O-alpha-D-glucosyl-N-ethylmoranoline.

EXAMPLE 1

The mixture (18.6 g) obtained in Reference Example 1 was dissolved in 125 ml of hot ethanol and the solution was cooled to room temperature. To this was added 13.5 gm of p-toluenesulphonic acid (p-CH$_3$C$_6$H$_4$SO$_3$H.-H$_2$O). The mixture was allowed to stand at 5° C. for 3 days after the addition of 125 ml of acetone. The resulting crystals were collected by filtration and gently washed with cold ethanol followed by drying to give 11.3 g of crystals. Yield: 72.8%.

The resulting crystals were analyzed by a silica gel thin layer chromatography (Art. 5554, Merck & Co; developer is a mixture of n-propanol:concentrated ammonia water:water in a ratio of 6:2:1; colorized by aqueous solution of potassium permanganate) and it was found that the crystals were composed solely of 4-O-alpha-D-glucosylmoranoline p-toluenesulphonate (R$_f$ = 0.16).

This was dried at 70° C. for 10 hours in vacuo and the physical data was measured.

Melting point: 127°–131° C. $[\alpha]^{25}_D = +79.6°$ (c = 1.0%, water). Elem. Anal: C$_{12}$H$_{23}$NO$_9$

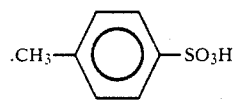

(C$_{19}$H$_{31}$NO$_{12}$S)

Calcd: C:45.87; H:6.28; N:2.82.
Found: C:45.50; H:6.71; N:2.67.

The crystals were dissolved in water, the solution was treated with a strongly basic ion exchange resin—Amberlite IRA-410 (OH$^-$)—to remove p-toluenesulphonic acid, and analyzed by high performance liquid chromatography by the same conditions as mentioned before to confirm that they are 4-O-alpha D-glucosylmoranoline of 99.2% purity.

This was dried in vacuo at 70° C. for 10 hours to measure the physical data.

Melting point: 189°–192° C. $[\alpha]^{25}_D = +128.6°$ (c = 1.0%, water).

Elem. Anal: C$_{12}$H$_{23}$NO$_9$ . 0.1H$_2$O
Calcd: C:44.06; H:7.15; N:4.28.
Found: C:44.17; H:7.54; N:4.31.

EXAMPLE 2

The mixture (1 g) obtained in Reference Example 2 was dissolved in 30 ml of hot ethanol, 1.1 g of benzenesulphonic acid (C$_6$H$_5$SO$_3$H.H$_2$O) was dissolved therein, and the solution was allowed to stand at 5° C. for 3 days. The resulting crystals were collected by filtration and gently washed with cold ethanol followed by drying to give 650 mg of crystals. Yield: 70.7%.

The resulting crystals were analyzed by a silica gel thin layer chromatography (Art. 5554, Merck & Co; developer used was n-propanol:conc ammonia water:-water of 6:2:1 mixing ratio; colorized by aqueous solution of potassium permanganate) and it was confirmed that the crystals were composed solely of 4-O-alpha D-glucosyl-N-methylmoranoline benzenesulphonate (R$_f$ = 0.31).

This was dried in vacuo at 80° C. for 10 hours and subjected to a measurement of physical data. Melting point 142°–145° C.

$[\alpha]^{25}_D = +59.9°$ (c = 1.7%, water).

Elem. Anal: C$_{13}$H$_{25}$NO$_9$

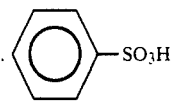

(C$_{19}$H$_{31}$NO$_{12}$S)

Calcd: C:45.87; H:6.28; N:2.82.
Found: C:45.78; H:6.52; N:2.88.

The crystals were dissolved in water, the solution was treated with Amberlite IRA-410 (OH$^-$), a strongly basic ion exchange resin, to remove benzenesulphonic acid, and analyzed by a high performance liquid chromatography at the conditions as given above to confirm that they are 4-O-alpha-D-glucosyl-N-methylmoranoline of 99.2% purity.

This was dried at 70° C. for 10 hours in vacuo and subjected to a measurement for physical data.

Melting point: 172.0° C. $[\alpha]^{25}_D = +104.7°$ (c = 1.0%, water).

ELEM. Anal: C$_{13}$H$_{25}$NO$_9$
Calcd: C:46.01; H:7.43; N:4.13.
Found: C:45.74; H:7.60: N:4.08.

EXAMPLE 3

The mixture (5 g) obtained in Reference Example 2 was dissolved in 200 ml of methanol and the solution was stirred with a solution of 4.5 g of p-toluenesulphonic acid in methanol. Then the mixture was allowed to stand overnight at 5° C. The resulting crystals were collected, gently washed with cold methanol, and dried to give 4.6 g of crystals. Yield: 97.2%.

A portion (about 100 mg) of the crystals was dissolved in water, passed through 5 ml of Amberlite IRA-410 (OH$^-$), a strongly basic ion exchange resin, to remove p-toluenesulphonic acid, washed with water, then both the passed solution and the washings were concentrated in vacuo and analyzed by a high performance liquid chromatography at the same conditions as above to confirm that it was 4-O-alpha-D-glucosyl-N-methyl-moranoline of 98.7% purity.

The product (4.2 g) was passed through 70 ml of Amberlite IRA-410 (OH$^-$) followed by washing with water. Both the passed solution and the washings were combined, water was removed therefrom in vacuo, and 2.7 g of solids were obtained. This was dissolved in 50 ml of methanol, stirred with a solution of 1.7 g of p-toluenesulphonic acid in 50 ml of methanol, and allowed to stand overnight at 5° C..

The resulting crystals were collected and gently washed with cold ethanol followed by drying to give 3.9 g of crystals.

The operation was repeated once again to give 3.6 g of 4-O-alpha-D-glucosyl-N-methylmoranoline p-toluenesulphonate.

This was treated with Amberlite IRA-410 (OH$^-$) as above and analyzed by a high performance liquid chromatography to find that the purity was 99.97%. This was dried at 80° C. for 10 hours in vacuo and physical data were measured.

Melting point: 223°–225° C. $[\alpha]^{25}_D = +74.5°$ (c = 0.8%, water)

Elem. Anal: C$_{13}$H$_{25}$NO$_9$

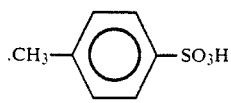

($C_{20}H_{33}NO_{12}S$)
Calcd: C:46.96; H:6.50; N:2.74.
Found: C:46.76; H:6.84; N:2.66.

EXAMPLE 4

The mixture (5 g) obtained in Reference Example 2 was dissolved in 50 ml of methanol, a solution of 6.6 g of 2,4-dimethylbenzenesulphonic acid in 50 ml of methanol was added thereto, and stirred with 100 ml more of ethanol. This was allowed to stand at 5° C. for 3 days. The resulting crystals were collected, gently washed with cold ethanol, and dried to give 3.5 g of crystal. Yield: 72.0%.

A portion (100 mg) of the crystals was treated with Amberlite IRA-410 (OH$^-$), as in Example 3, and analyzed by high performance liquid chromatography to confirm that it was 4-O-alpha-D-glucosyl-N-methylmoranoline of 95.8% purity.

For further analysis, the product (500 mg) was dissolved in a hot mixture of 7 ml of methanol and 0.4 ml of water and the solution was allowed to stand overnight at room temperature. The resulting cyrstals were collected and dried to give 330 mg of crystals. This was dried at 70° C. for 10 hours in vacuo and subjected to a physical data measurement.

Melting point: 219°–221° C. $[\alpha]^{25}_D = +69.6°$ (c=1.1%, water).

Elem. Anal: $C_{13}H_{25}NO_9$

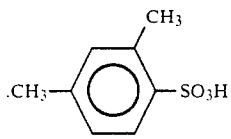

($C_{21}H_{35}NO_{12}S$)
Calcd: C:47.99; H:6.71; N:2.67.
Found: C:47.88; H:7.04; N:2.65.

Result of analysis by a high performance liquid chromatography at the same conditions as above revealed that its purity was 99.8%.

EXAMPLE 5

The mixture (2.3 g) obtained in Reference Example 3 was dissolved in 20 ml of methanol and 8.85 g of p-toluenesulphonic acid and methanol were added thereto. Methanol was removed therefrom in vacuo and the residue was again dissolved in a hot mixture of 100 ml of methanol and 100 ml of ethanol. The solution was concentrated in vacuo whereupon cyrstals began to appear and, at that stage, the concentration was stopped and allowed to stand at 5° C. for 2 days. The crystals were collected, softly washed with cold ethanol, and dried to give 2.6 g of crystals. Yield: 76.0%.

Melting point: 173°–178° C. $[\alpha]^{25}_D = +63.6°$ (c=1.2%, water)

Elem. Anal: $C_{14}H_{27}NO_9$

($C_{21}H_{35}NO_{12}S$)
Calcd: C:47.99; H:6.71; N:2.67.
Found: C:47.75; H:7.08; N:2.70.

A portion (100 mg) of the crystals was treated with Amberlite IRA-410 (OH$^-$), a strongly basic ion exchange resin, as in Example 3, and analyzed by high performance liquid chromatography to confirm that it was 4-O-alpha-D-glucoosyl-N-ethylmoranoline of 99.0% purity. This was dried at 70° C. for 10 hours in vacuo and physical data were measured.

Melting point: 118°–120° C. $[\alpha]^{25}_D = +83.3°$ (c=1.0%, water)

Elem. Anal: $C_{14}H_{27}NO_9 \cdot 2H_2O$
Calcd: C:43.18; H:8.02; N:3.60.
Found: C:43.61; H:7.94; N:3.93.

REFERENCE EXAMPLE 4

4-O-alpha-D-glucosylmoranoline (5 g) was dissolved in 13.3 g of 35% formaldehyde and the solution was refluxed at 110° C. for 3 hours. After the reaction, water and formaldehyde were removed in vacuo, the residue was dissolved in 150 ml of methanol, then 8.8 g of sodium borohydride was added in an ice bath, and the mixture was stirred overnight at room temperature. After the reaction, 40 ml of acetic acid was added, the mixture was concentrated in vacuo, and the concentrate was passed through 200 ml of Amberlite IRA-410 (OH$^-$), a strongly basic ion exchange resin. The passed solution was then passed through 200 ml of Dowex 50 W×2 (H$^+$), a strongly acidic ion exchange resin, to cause adsorption. This was thoroughly washed with water, eluted with 0.5N ammonia water, the eluate was evaporated to remove the solvent in vacuo, and the residue was dried to give 4.5 g of powder.

This was analyzed by high performance liquid chromatography, as in Example 1, and was found to be composed of 32.9% of unreacted 4-O-alpha-D-glucosylmoranoline and 67.1% of 4-O-alpha-D- glucosyl-N-methylmoranoline.

EXAMPLE 6

The powder (4.5 g) obtained in Reference Example 4 was dissolved in 120 ml of methanol and allowed to stand overnight at room temperature after addition of 4 g of p-toluenesulphonic acid. The resulting crystals were collected by filtration and dried to give 5.1 g of crystals.

This was analyzed by high performance liquid chromatography, as above, and found to be composed of 1.8% of unreacted 4-O-alpha-D-glucosylmoraline and 98.2% of 4-O-alpha-D-glucosyl-N-methylmoranoline. In order to obtain pure product, this was dissolved again, the solution was passed through 50 ml of Amberlite IRA-410 (OH$^-$), a strongly basic ion exchange resin, then washed with water, the washings were combined with the passed solution, water was evaporated therefrom in vacuo, the residue was dissolved in methanol, 2.3 g of p-toluenesulphonic acid was added to the solution, the mixture was allowed to stand overnight at room temperature, and the resulting crystals were collected by filtration and dried to give 4.3 g of the product. This was analyzed by high performance liquid chromatography, as above, and found to be pure 4-O-alpha-D-glucosyl-N-methylmoranoline.

The Examples illustrate presently preferred conditions of operation. In general, a wide range of proportions of arylsulfonic acid to (I), (II) and/or (III) may be used. For example, the amount of the arylsulfonic acid may range from about 1 to about 5 mols of arylsulfonic acid per mol of (I), (II) and/or (III) in the solution. For purposes of determining the amount of arylsulfonic acid to be used the mols of (II) and (III) are calculated as $$M \times \frac{A}{B} \text{ or } N \times \frac{A}{C}$$

where M and N are the mols of (II) or (III), respectively, in solution, A is the molecular weight of (I) and B and C are the molecular weights of (II) and (III), respectively.

We claim:

1. A process of preparing crystals of a glucosylmoranoline represented by the formula (III)

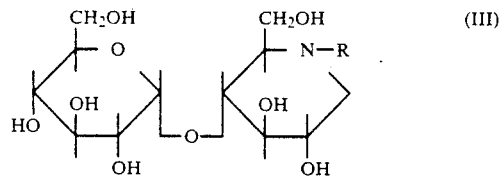

wherein R is hydrogen or lower alkyl, which comprises contacting a solution in a polar solvent of (i) a mixture of a moranoline derivative represented by the formula (I)

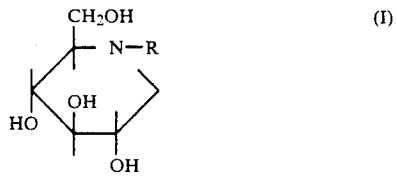

wherein R is as defined above, said glucosylmoranoline (III) and an oligoglucosylmoraline represent by the formula (II)

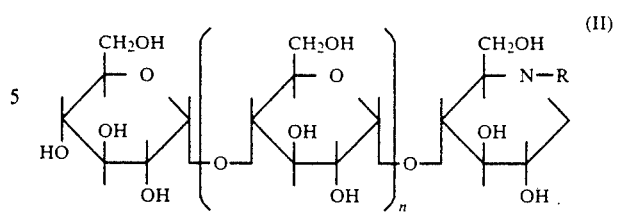

wherein R is as defined above and n is an integer from 1 to about 20 or (ii) a mixture of said (I) and said (III) with an arylsulphonic acid, and collecting crystals that are crystallized out of said solution.

2. The process according to claim 1, wherein said polar solvent is water or an organic polar solvent.

3. The process according to claim 2, wherein said polar solvent is a water-miscible organic solvent.

4. The process according to claim 2, wherein said polar solvent is water, methanol, ethanol or isopropanol or a mixture of two or more thereof.

5. The process according to claim 1, wherein said arylsulfonic acid is a substituted or unsubstituted benzenesulfonic acid or an alkyl-substituted or unsubstituted dicyclic or tricylic arylsulfonic acid.

6. The process according to claim 5, wherein said arylsulfonic acid is a lower alkyl-substituted or unsubstituted benzenesulfonic acid.

7. The process according to claim 5, wherein said arylsulfonic acid is benzenesulfonic acid, p-toluenesulfonic acid or 2,4-dimethylbenzenesulfonic acid.

8. A process of separating a mixture of a glucosylmoranoline represented by the formula (III)

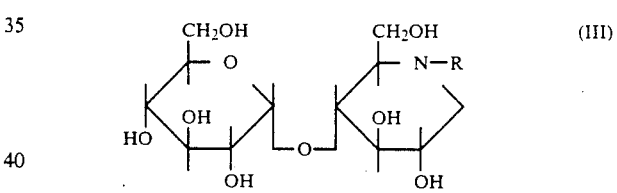

in which R is hydrogen and a glucosylmoranoline of formula (III) wherein R is methyl, which comprises contacting a solution of said mixture in a polar solvent with an arylsulfonic acid, and collecting crystals of said glucosylmoranoline (III) wherein R is hydrogen.

9. The process according to claim 8 wherein said polar solvent is water, methanol, ethanol or isopropanol or a mixture of two or more thereof.

10. The process according to claim 8 wherein said arylsulfonic acid is benzenesulfonic acid, p-toluenesulfonic acid or 2,4-dimethylbenzenesulfonic acid.

11. The process according to claim 1, wherein any arylsulfonic acid in said collected crystals is removed therefrom.

12. The process according to claim 8, wherein any arylsulfonic acid in said collected crystals is removed therefrom.

* * * * *